United States Patent [19]

Blank

[11] 4,166,070

[45] Aug. 28, 1979

[54] PROCESS FOR THE PREPARATION OF SULFONIC ACID CHLORIDES

[75] Inventor: Heinz U. Blank, Odenthal, Fed. Rep. of Germany

[73] Assignee: Bayer Aktiengesellschaft, Leverkusen, Fed. Rep. of Germany

[21] Appl. No.: 817,456

[22] Filed: Jul. 19, 1977

[30] Foreign Application Priority Data

Aug. 5, 1976 [DE] Fed. Rep. of Germany ....... 2635279
May 12, 1977 [DE] Fed. Rep. of Germany ....... 2721429

[51] Int. Cl.$^2$ .......................................... C07C 143/70
[52] U.S. Cl. ................................................ 260/543 R
[58] Field of Search .................................... 260/543 R

[56] References Cited

U.S. PATENT DOCUMENTS

3,701,806 10/1972 Keogh et al. .................... 260/543 R

Primary Examiner—Gerald A. Schwartz
Attorney, Agent, or Firm—Sprung, Felfe, Horn, Lynch & Kramer

[57] ABSTRACT

A process for the preparation of a sulfonic acid chloride of the formula

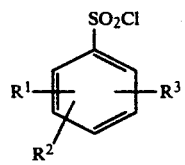

wherein
R$^1$, R$^2$ and R$^3$ are identical or different and denote hydrogen, a lower alkyl or cycloalkyl radical, halogen, aryl, aralkyl, aryl-ether or one of the radicals

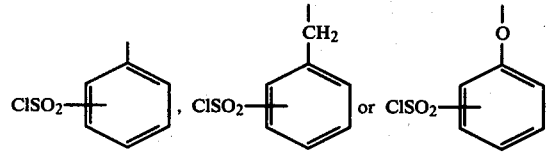

or where
adjacent radicals R$^1$ and R$^2$ are linked to form a cycloaliphatic or aromatic carbocyclic ring which is optionally substituted by a sulfonic acid chloride group which comprises contacting an aromatic compound of the formula

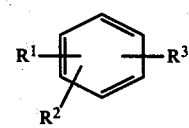

wherein
R$^1$, R$^2$ and R$^3$ have the previously assigned significance with an approximately equimolar amount of a sulfonating agent, based upon the number of sulfonic acid chloride groups to be introduced and an excess of thionyl chloride, the sulfonating agent and thionyl chloride being initially introduced or added simultaneously with the addition of said aromatic compound.

23 Claims, No Drawings

PROCESS FOR THE PREPARATION OF SULFONIC ACID CHLORIDES

The invention relates to a process for the preparation of sulphonic acid chlorides by reacting aromatic compounds with a sulphonating agent and thionyl chloride.

It is known (Ullmanns Enzyklopädie der technischen Chemie (Ullmann's Encyclopaedia of Industrial Chemistry), 4th edition, volume 8 (1974), page 420) to prepare benzenesulphonic acid chloride by reacting benzene with excess chlorosulphonic acid. The use of excess chlorosulphonic acid is, in particular with regard to the protection of the environment, a considerable disadvantage of this process since the excess chlorosulphonic acid is hydrolysed during the working-up of the reaction mixture with water to give hydrogen chloride and sulphuric acid and is obtained as so-called dilute acid together with the sulphuric acid also additionally formed as a by-product and together with considerable amounts of benzenesulphonic acid which has not been converted to the sulphonic acid chloride. The working-up and removal of this dilute acid unavoidably obained leads to considerable expenditure. On simple neutralisation of the dilute acid a corresponding salt content of the effluent results, which is also undesirable for reasons of environmental protection and makes an expensive desalination of the effluent necessary.

A process has now been found for the preparation of sulphonic acid chlorides of the formula

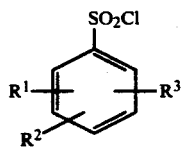

wherein

R$^1$, R$^2$ and R$^3$ are identical or different and denote hydrogen, a lower alkyl or a cycloalkyl radical, halogen, aryl, aralkyl, aryl-ether or a radical

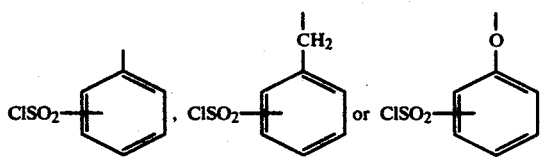

or where adjacent radicals R$^1$ and R$^2$ are linked to form a cycloaliphatic or aromatic carbocyclic ring which is optionally substituted by a sulphonic acid chloride group, according to which an aromatic compound of the formula

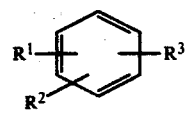

(II)

wherein

R$^1$, R$^2$ and R$^3$ have the abovementioned meaning is reacted with about the equimolar amount of a sulphonating agent, relative to each sulphonic acid chloride group to be introduced, and an excess of thionyl chloride, the sulphonating agent and the thionyl chloride being initially introduced or being added simultaneously with the aromatic compound.

Lower alkyl radicals (R$^1$ to R$^3$) can be straight-chain or branched alkyl radicals with 1 to 6, preferably 1 to 4, carbon atoms. Examples which may be mentioned are methyl, ethyl, propyl, iso-propyl, butyl, iso-butyl, pentyl, iso-pentyl, hexyl and iso-hexyl.

Cycloalkyl radicals (R$^1$ to R$^3$) which may be mentioned are, for example, cyclopentyl and cyclohexyl, preferably cyclohexyl.

Fluorine, chlorine, bromine and iodine, preferably fluorine, chlorine and bromine, may be mentioned as halogens (R$^1$ to R$_3$).

Aryl radicals (R$^1$ to R$^3$) which may be mentioned are, for example, phenyl and naphthyl, preferably phenyl.

Possible aralkyl radicals (R$^1$ to R$^3$) are, for example, those with 6 to 18 carbon atoms, the aliphatic part of which contains 1 to 6 carbon atoms and the aromatic part of which is a radical from the benzene series. The following araliphatic radicals may be mentioned as examples: benzyl, β-ethylphenyl, γ-propyl-phenyl and β-phenyl-n-hexyl, preferably benzyl.

An aryl-ether radical (R$^1$ to R$^3$) which may be mentioned is, in particular, the phenoxy radical.

Fused ring systems, such as indane, tetralin, indene and naphthalene, preferably naphthalene, are formed by linking the adjacent radicals R$^1$ and R$^2$ to give a cycloaliphatic or aromatic ring.

It is, of course, possible that the radicals R$^1$ to R$^3$ are substituted by further radicals which are not modified under the conditions of the process according to the invention.

Examples which may be mentioned are:

Halogen, lower alkyl, e.g., of C$_1$ to C$_6$; aryl, e.g., of C$_6$ to C$_{12}$; aroxy, e.g., C$_6$ to C$_{12}$; alkoxy, e.g., C$_1$ to C$_3$. When the substituent is aralkyl, the alkyl portion preferably has 1 to 4 carbon atoms in the chain.

Preferred aromatic compounds which may be mentioned are compounds of the formula

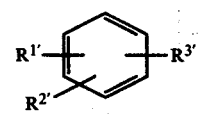

wherein

R$^{1'}$, R$^{2'}$ and R$^{3'}$ are identical or different and denote hydrogen, an alkyl radical with 1 to 4 carbon atoms, fluorine, chlorine, bromine, phenyl, phenoxy or benzyl or where adjacent radicals R$^{1'}$ and R$^{2'}$ are linked to form a cycloaliphatic or aromatic carbocyclic ring with 6 ring members.

The following aromatic compounds may be mentioned as examples: benzene, toluene, ethylbenzene, isopropylbenzene (cumene), tetralin, o-xylene, m-xylene, p-xylene, diphenyl, diphenylmethane, chlorobenzene, 1-chloronaphthalene, 2-chloronaphthalene, o-chlorotoluene, 1,2-, 1,3- and 1,4-dichlorobenzene, 2,3-, 2,4-, 2,5-, 3,4- and 2,6-dichloro-toluene, 2,3-, 2,4-, 2,6-, 3,4- and 2,5-dimethylchlorobenzene, bromobenzene, fluorobenzene, 1,2,3- and 1,2,4-trichlorobenzene, diphenyl ether, naphthalene, 1- and 2-methylnaphthalene and 2-, 3- and 4-bromotoluene.

Sulphonating agents which may be mentioned are sulphuric acid, sulphur trioxide and chlorosulphonic acid, preferably chlorosulphonic acid. Mixtures of the sulphonating agents, for example oleum, can also be employed.

In the process according to the invention, the sulphonating agent can be employed in about equimolar amounts to the aromatic compound, relative to each sulphonic acid chloride group to be introduced. However, it can also be advantageous to use the aromatic compound in a slight excess of up to about 1.3 mols, preferably up to 1.2 mols and particularly preferably up to 1.1 mols, relative to each sulphonic acid chloride group to be introduced, depending on the sulphone formation occurring as a side reaction to a small extent. About equimolar amounts are preferably employed.

It can also be advantageous to employ the aromatic compound in an amount which is slightly lower than the molar amount for each sulphonic acid chloride group to be introduced, that is to say about 0.7 mol, preferably 0.8 mol and particularly preferably 0.9 mol, relative to the sulphonating agent, and to separate off the slight excess of sulphonating agent, in particular chlorosulphonic acid, for example by distillation, or to concentrate it and optionally to recycle it.

The thionyl chloride can be employed in the process according to the invention without particular purification.

By the process according to the invention, the thionyl chloride is employed in excess to the aromatic compound. In general, an amount of up to 10 mols of thionyl chloride per mol of the aromatic compound is employed. If, for example, chlorosulphonic acid is used as the sulphonating agent, about 1.05 to 5, preferably 1.2 to 3 and particularly preferably 1.5 to 2, mols of thionyl chloride, relative to each sulphonic acid chloride group to be introduced, are employed per mol of the aromatic compound. If, for example, sulphuric acid is used as the sulphonating agent, about 2.1 to 10, preferably 2.5 to 6 and particularly preferably 3 to 4, mols of thionyl chloride are used per mol of aromatic compound.

In the process according to the invention, the excess thionyl chloride can at the same time be employed as the solvent. However, it is also possible to carry out the process according to the invention in the presence of other solvents or diluents which are inert under the reaction conditions. Such solvents or diluents which may be mentioned are: sulphur dioxide and sulphuryl chloride, hydrocarbons and halogenohydrocarbons, in particular alkanes and halogenoalkanes, such as chloroform, carbon tetrachloride, methylene chloride, di-, tri- and tetra-chloroethylene, di-, tri-, tetra- and penta-chloroethane, 1,1,2-trichloro-1,2,2-trifluoroethane and tetra-fluoroethylene.

In general, the process according to the invention is carried out in a temperature range from about 10° to 90° C., preferably from 20° to 80° C. and particularly preferably from 30° to 70° C.

The process according to the invention can be carried out both under normal pressure and under reduced pressure or under elevated pressure up to 10 bars, preferably up to 5 bars. If the reaction temperature is chosen higher than the boiling point of thionyl chloride under normal pressure, the reaction is advantageously carried out under a pressure which corresponds to the vapour pressure of thionyl chloride under the particular reaction conditions chosen.

In the process according to the invention it is possible to initially introduce all or part of the sulphonating agent and (a) simultaneously to introduce all or part of the thionyl chloride and to add the aromatic compound and any remaining sulphonating agent and/or remaining thionyl chloride, any remaining thionyl chloride being added as a function of the amount of thionyl chloride already initially introduced in such a way that the total amount of thionyl chloride employed in the reaction at least corresponds to the amount of aromatic compound added, or (b) to add the aromatic compound and thionyl chloride and any remaining sulphonating agent, thionyl chloride being added at a rate approximately corresponding to the conversion of the aromatic compound to the sulphochloride, or also more rapidly, and the addition taking place, in each case, so that the sulphonating agent is always introduced into the reaction mixture before the corresponding amount of the aromatic compound.

In general, the process according to the invention is carried out by warming the appropriate amount of sulphonating agent and thionyl chloride to the chosen reaction temperature and then adding a small amount of the aromatic compound. After the reaction has started, the remainder of the aromatic compound, and, if appropriate, futher thionyl chloride, is then added, preferably in accordance with the rate of the conversion of the aromatic compound to the sulphonic acid chloride.

However, it is also possible to initially introduce only the sulphonating agent and to add the aromatic compound and the thionyl chloride simultaneously, according to the chosen overall ratio, either in separate streams or after previous mixing.

In a preferred embodiment, the sulphonating agent and the thionyl chloride are initially introduced and the aromatic compound is added in accordance with the rate of its conversion to the sulphonic acid chloride.

The amounts of hydrogen chloride and sulphur dioxide formed as by-products in the process according to the invention are removed in the customary manner and can optionally be employed in other reactions.

The end of the reaction can be detected by the fact that the evolution of gas stops, or by known analytical methods. Thereafter, the excess thionyl chloride and, if appropriate, unconverted aromatic compound, or unconverted chlorosulphonic acid are separated off, preferably by fractional distillation.

The resulting reaction mixtures are preferably worked up by fractional distillation under normal or reduced pressure, preferably under reduced pressure, especially in the preparation of aromatic mono-sulphonic acid chlorides. In general, the unconverted thionyl chloride, chlorosulphonic acid, if appropriate, and the unconverted aromatic compound are distilled off in the pressure range from 1 to 760 mm Hg and the sulphonic acid chloride is obtained on further distillation in the pressure range from 0.1 to 15 mm Hg, preferably from 0.5 to 10 mm Hg.

The process according to the invention can be carried out both discontinuously and continuously. When the process according to the invention is carried out continuously, the unconverted starting materials, in particular thionyl chloride, are optionally re-employed in the process.

Aromatic sulphonic acid chlorides can advantageously be prepared by the process according to the invention in good yields relative to the aromatic compound and, when chlorosulphonic acid is used as the sulphonating agent, in particular also relative to the chlorosulphonic acid.

In contrast to known processes, in the process according to the invention the reaction mixture can be worked up by distillation. By the process according to the invention, the dilute acid unavoidably obtained and the ecological problems associated with it are substantially done away with.

The sulphonic acid chlorides prepared by the process according to the invention are intermediate products, for example for dyestuffs.

EXAMPLES

Example 1 to 24

A mixture of thionyl chloride and chlorosulphonic acid of the composition indicated in Tables I and II which follow is initially introduced into a flask, provided with a stirrer, a reflux condenser with an off-gas outlet and a dropping funnel and an internal thermometer, at the reaction temperature indicated in the tables.

The amount of benzene indicated in Table I which follows or, in Table II, another aromatic compound, is slowly added dropwise from the dropping funnel in the course of 4 hours, the reaction temperature being maintained by additional heating.

After the addition of the aromatic compound has ended, the mixture is subsequently stirred at the temperature indicated until the evolution of gas has ended.

The excess thionyl chloride and, if appropriate, unconverted aromatic compound are then distilled off in a rotary evaporator under 100 mm Hg.

The remaining liquid residue is then subjected to fractional distillation under 10 mm Hg. The amounts of the aromatic sulphonic acid chlorides indicated in Tables I and II which follow are obtained as colourless to slightly yellowish coloured compounds.

Table I

| Example No. | SOCl$_2$ g (mols) | ClSO$_3$H g (mols) | Benzene g (mols) | Temperature °C. | Benzenesulphonyl chloride g | Purity+ | % of theory++ |
|---|---|---|---|---|---|---|---|
| 1 | 381 (3.2) | 187 (1.6) | 124 (1.6) | 30 | 226.1 | 98.9% | 79 |
| 2 | 381 (3.2) | 187 (1.6) | 124 (1.6) | 50 | 223.3 | 99.5% | 79 |
| 3 | 381 (3.2) | 187 (1.6) | 156 (2.0) | 30 | 204.0 | 97.6% | 71 |
| 4 | 381 (3.2) | 187 (1.6) | 156 (2.0) | 50 | 231.0 | 98.5% | 81 |
| 5 | 381 (3.2) | 187 (1.6) | 140 (1.8) | 70 | 222.3 | 98.9% | 78 |
| 6 | 333 (2.8) | 187 (1.6) | 124 (1.6) | 50 | 218.0 | 98.7% | 76 |
| 7 | 238 (2.0) | 187 (1.6) | 124 (1.6) | 50 | 213.0 | 99.3% | 75 |

+ according to analysis by gas chromatography
++ relative to ClSO$_3$H

Table II

| Example No. | Aromatic compound | | SOCl$_2$ g (mols) | ClSO$_3$H g (mols) | Temperature °C. | Aromatic sulphochloride | | |
|---|---|---|---|---|---|---|---|---|
| | g | (mols) | | | | g | Purity+ | % of theory |
| 8 | Toluene | | | | | | Toluenesulphonyl chloride | |
| 8a | 147 | (1.6) | 381 (3.2) | 187 (1.6) | 10 | 117 | 19.2% o-  80.8% p- | 38 |
| 8b | 147 | (1.6) | 381 (3.2) | 187 (1.6) | 30 | 263 | 17.8% o-  79.3% p- | 84 |
| 9 | Ethylbenzene | | | | | | Ethylbenzenesulphonyl chloride | |
| | 106 | (1.0) | 238 (2.0) | 116 (1.0) | 40 | 164 | 16.3% o- | 80 |
| 10 | Cumeme | | | | | | 4-Isopropyl-benzenesulphonyl chloride | |
| | 120 | (1.0) | 238 (2.0) | 116 (1.0) | 50 | 165 | 94.5% | 72 |
| 11 | Tetralin | | | | | | 1,2,3,4-Tetrahydronaphthalene-6-sulphonyl chloride | |
| | 132 | (1.0) | 238 (2.0) | 116 (1.0) | 50 | 161 | 95.1% | 70 |
| 12 | o-Xylene | | | | | | 3,4-Dimethylbenzenesulphonyl chloride | |
| | 106 | (1.0) | 238 (2.0) | 116 (1.0) | 40 | 114 | 95.9% | 54 |
| 13 | m-Xylene | | | | | | 2,4-Dimethylbenzenesulphonyl chloride | |
| | 106 | (1.0) | 238 (2.0) | 116 (1.0) | 40 | 125 | 98.1% | 61 |
| 14 | p-Xylene | | | | | | 2,5-Dimethylbenzenesulphonyl chloride | |
| | 106 | (1.0) | 238 (2.0) | 116 (1.0) | 50 | 194 | 93.0%++ | 88 |
| 15 | Diphenyl | | | | | | 4,4'-Diphenyldisulphonyl chloride++ | |
| | 154 | (1.0) | 476 (4.0) | 232 (2.0) | 50 | 227 | Melting point 199° C. | 65 |
| 16 | Diphenylmethane | | | | | | Diphenylmethane-4,4'-disulphonyl chloride++ | |
| | 168 | (1.0) | 476 (4.0) | 232 (2.0) | 40 | 224 | Melting point 121°0 C. | 61 |
| 17 | Chlorobenzene | | | | | | p-Chlorobenzenenesulphonyl chloride | |
| | 180 | (1.0) | 381 (3.2) | 187 (1.6) | 55 | 278 | 97.6% | 82 |
| 18 | Chloronaphthalene (purity 92%) | | | | | | 4-Chloronaphthalene-1-sulphonyl chloride | |
| | 250 | (1.54) | 381 (3.2) | 164 (1.4) | 40 | 315 | uniform according to thin layer chromatography | 85 |
| 19 | o-Chlorotoluene | | | | | | 2-Chloro-4-methyl-benzenesulphonyl chloride | |
| | 203 | (1.6) | 381 (3.2) | 187 (1.6) | 40 | 297 | 98.2% | 81 |
| 20 | 1,2-Dichlorobenzene | | | | | | 3,4-Dichloro-benzenesulphonyl chloride | |
| | 235 | (1.6) | 381 (3.2) | 187 (1.6) | 50 | 334 | 99.1% | 85 |
| 21 | 2,6-Dichloro-toluene | | | | | | 2,4-Dichloro-3-methyl-benzenesulphonyl chloride | |
| | 161 | (1.0) | 238 (2.0) | 116 (1.0) | 50 | 179 | 91.0% | 63 |
| 22 | 2,5-Dimethyl-chloro-benzene | | | | | | 2,5-Dimethyl-4-chloro-benzenesulphonyl chloride++ | |

Table II-continued

| Example No. | Aromatic compound g | (mols) | SOCl₂ g (mols) | ClSO₃H g (mols) | Temperature °C. | Aromatic sulphochloride g | Purity+ | % of theory |
|---|---|---|---|---|---|---|---|---|
|  | 141 | (1.0) | 238 (2.0) | 116 (1.0) | 40 | 192 (recrystallised) | Melting point 48° C. | 80 |
| 23 | Bromobenzene 157 | (1.0) | 238 (2.0) | 116 (1.0) | 60 | 197 | p-Bromo-benzenesulphonyl chloride 99.1% | 77 |
| 24 | Fluorobenzene 96 | (1.0) | 238 (2.0) | 116 (1.0) | 60 | 149 | p-Fluoro-benzenesulphonyl chloride 94.5% | 72 |

+according to analysis by gas chromatography
++instead of distillation, working-up by pouring into water, isolating and recrystallising.

Example 25

A mixture of 480 g (4.0 mols) of thionyl chloride and 160 g (1.6 mols) of sulphuric acid is kept at 50° C. for 90 minutes in the apparatus described in Example 1 and 124 g (1.6 mols) of benzene are then added in the course of 4 hours at the same temperature.

The reaction mixture is then subsequently stirred for one hour at 80° C.

Excess thionyl chloride is then distilled off in a rotary evaporator under 20 mm Hg and the liquid residue is distilled over a distillation bridge under 5 mm Hg.

223.5 g of benzenesulphonyl chloride are obtained with 99.3% purity (according to analysis by gas chromatography); this corresponds to a yield of 79% of theory.

Example 26

187 g (1.6 mols) of chlorosulphonic acid are initially introduced into the apparatus described in Example 1.

A mixture of 124 g (1.6 mols) of benzene and 381 g (3.2 mols) of thionyl chloride is added dropwise at 30° C. in the course of 6 hours and the reaction mixture is then subsequently stirred for 30 minutes at 50° C.

Excess thionyl chloride is distilled off in a rotary evaporator under 200 mm Hg and the liquid residue is distilled over a distillation bridge under 2 mm Hg.

208.3 g of benzenesulphonyl chloride are obtained with a purity of 98% (according to analysis by gas chromatography); this corresponds to a yield of 72% of theory.

Example 27 (comparison example)

124 g (1.6 mols) of benzene and 381 g (3.2 mols) of thionyl chloride are initially introduced into the apparatus described in Example 1 and 187 g (1.6 mols) of chlorosulphonic acid are added at 30° C. in the course of 4 hours, whilst stirring. The mixture is subsequently stirred for a further hour at 50° C. and the excess thionyl chloride is then distilled off in a rotary evaporator under a pressure of 15 to 20 mm Hg. Subsequent distillation over a distillation bridge under 5 mm Hg gives 140 g of distillate which, according to analysis by gas chromatography, contains only 59.2% of benzenesulphonyl chloride (remainder thionyl chloride and chlorosulphonic acid); this corresponds to a yield of only 29% of theory).

Example 28 (comparison example)

381 g (3.2 mols) of thionyl chloride are initially introduced into the apparatus described in Example 1, which was provided with a further dropping funnel.

124 g (1.6 mols) of benzene and 187 g (1.6 mols) of chlorosulphonic acid are simultaneously added dropwise in the course of 4 hours at 50° C. The mixture is subsequently stirred for a further 30 minutes at 50° C. and excess thionyl chloride is then stirred off in a rotary evaporator under a pressure of 20 mm Hg.

The residue is distilled over a distillation bridge under a pressure of 5 mm Hg.

130.3 g of distillate are obtained which, according to analysis by gas chromatography, contains 62.6% of benzenesulphonic acid chloride (remainder thionyl chloride and chlorosulphonic acid); this corresponds to a yield of only 38% of theory.

What is claimed is:

1. In a process for the preparation of a sulfonic acid chloride of the formula

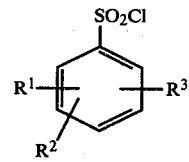

wherein

R¹, R² and R³ are identical or different and denote hydrogen, a lower alkyl or cycloalkyl radical, halogen, aryl, aralkyl, aryl-ether or one of the radicals

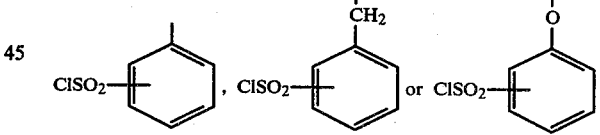

or where adjacent radicals R¹ and R² are linked to form a cycloaliphatic or aromatic carbocyclic ring which is optionally substituted by a sulfonic acid chloride group by contacting an aromatic compound of the formula

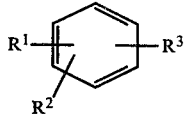

wherein

R¹, R² and R³ have the previously assigned significance with a sulfonating agent in the presence of thionyl chloride, the improvement which comprises employing an approximately equimolar amount of said sulfonating agent, based upon the number of sulfonic acid chloride groups to be introduced, employing an excess of thionyl chloride, the sulfonating agent and thionyl chloride being initially introduced or added simultaneously with the addition of said aromatic compound, said process further characterized in that:

A. the sulfonating agent and the thionyl chloride are initially introduced and the aromatic compound is added thereafter; or B. the sulfonating agent is initially introduced into a reaction zone and the aromatic compound and thionyl chloride are simultaneously added thereto thereafter; the process being carried out at a temperature in the range of 20° to 90° C.

2. A process according to claim 1 wherein the aromatic compound and thionyl chloride are added to the sulfonating agent in separate streams.

3. A process according to claim 1 wherein the aromatic compound and thionyl chloride are added to the sulfonating agent in the form of a mixture.

4. A process according to claim 1 wherein the thionyl chloride is employed in a stoichiometric excess of up to 10 mols per mol of aromatic compound.

5. A process according to claim 1 wherein the sulfonating agent is employed in an excess of up to about 1.3 mols per mol of aromatic compound relative to each sulfonic acid chloride group to be introduced.

6. A process according to claim 1 wherein after the reaction has ended, the reaction mixture is subjected to distillation.

7. A process according to claim 1 wherein the aromatic compound is toluene.

8. A process according to claim 1 wherein the aromatic compound is ethyl benzene.

9. A process according to claim 1 wherein the aromatic compound is cumene.

10. A process according to claim 1 wherein the aromatic compound is tetralin.

11. A process according to claim 1 wherein the aromatic compound is o-xylene.

12. A process according to claim 1 wherein the aromatic compound is m-xylene.

13. A process according to claim 1 wherein the aromatic compound is p-xylene.

14. A process according to claim 1 wherein the aromatic compound is diphenyl.

15. A process according to claim 1 wherein the aromatic compound is diphenylmethane.

16. A process according to claim 1 wherein the aromatic compound is chlorobenzene.

17. A process according to claim 1 wherein the aromatic compound is chloronaphthalene.

18. A process according to claim 1 wherein the aromatic compound is o-chlorotoluene.

19. A process according to claim 1 wherein the aromatic compound is 1,2-dichlorobenzene.

20. A process according to claim 1 wherein the aromatic compound is 2,6-dichlorotoluene.

21. A process according to claim 1 wherein the aromatic compound is 2,5-dimethylchlorobenzene.

22. A process according to claim 1 wherein the aromatic compound is bromobenzene.

23. A process according to claim 1 wherein the aromatic compound is fluorobenzene.

* * * * *

UNITED STATES PATENT AND TRADEMARK OFFICE
CERTIFICATE OF CORRECTION

PATENT NO. : 4,166,070
DATED : August 28, 1979
INVENTOR(S) : HEINZ U. BLANK

It is certified that error appears in the above-identified patent and that said Letters Patent are hereby corrected as shown below:

Column 1, line 23, "obained" should read -- obtained --.

Column 3, line 5, "the" should read -- these --.

Column 6, Table II, Example 9, Column headed "Purity +" under "16.3%" insert -- 83.7%p- --.

Column 6, Table II, Example 16, Column headed "Purity +" under "Melting point" insert -- (recrystallised) --.

Signed and Sealed this

Twenty-second Day of January 1980

[SEAL]

Attest:

SIDNEY A. DIAMOND

Attesting Officer

Commissioner of Patents and Trademarks